United States Patent [19]

Wahlig et al.

[11] Patent Number: 4,797,282
[45] Date of Patent: Jan. 10, 1989

[54] DRUG DEPOT CONTAINING CYTOSTATICS

[75] Inventors: Helmut Wahlig, Darmstadt; Elvira Dingeldein, Dreieich, both of Fed. Rep. of Germany

[73] Assignee: Merck Patent Gesellschaft Mit Beschrankter Haftung, Darmstadt, Fed. Rep. of Germany

[21] Appl. No.: 853,320

[22] Filed: Apr. 18, 1986

[30] Foreign Application Priority Data

Apr. 18, 1985 [DE] Fed. Rep. of Germany ....... 3513938

[51] Int. Cl.⁴ ............................................ A61F 13/00
[52] U.S. Cl. .................................... 424/422; 424/423; 424/424; 424/425; 424/426; 424/433
[58] Field of Search ............... 424/433, 422, 423, 424, 424/426, 425; 514/802

[56] References Cited

U.S. PATENT DOCUMENTS

| | | | |
|---|---|---|---|
| 3,826,678 | 7/1974 | Hoffman et al. | 424/423 X |
| 4,059,684 | 11/1977 | Gross et al. | 424/423 X |
| 4,191,740 | 3/1980 | Heusser et al. | 424/14 |
| 4,233,287 | 11/1980 | Heusser et al. | 424/14 |
| 4,321,117 | 3/1982 | Kaetsu et al. | 424/423 X |
| 4,536,387 | 8/1985 | Sakamoto et al. | 424/426 |
| 4,589,882 | 5/1986 | Urry | 424/423 |
| 4,610,692 | 9/1986 | Eitenmuller et al. | 424/423 X |
| 4,619,913 | 10/1986 | Luck et al. | 514/802 |

*Primary Examiner*—Thurman K. Page
*Attorney, Agent, or Firm*—Millen & White

[57] ABSTRACT

A drug depot, which can be implanted in the body, for the controlled, delayed release of cytostatics, comprises a synthetic material based on polyacrylates and/or polymethacrylates containing a cytostatic and at least one amino acid. The depot can be used in a particularly advantageous manner for the local control of tumors.

21 Claims, No Drawings

DRUG DEPOT CONTAINING CYTOSTATICS

BACKGROUND OF THE INVENTION

The invention relates to a drug depot, which can be implanted in the body, for the controlled, delayed release of cytostatics.

Large numbers of materials which can be implanted in the body and contain cytostatics are known. The basic materials which have been mentioned are both organic polymers such as, for example, polyglycolides, polylactides, silicone rubber, polycarboxylic acids, collagen or gelatin, and inorganic materials such as, for example, sintered or compressed tricalcium phosphate.

The materials which have hitherto been proposed are intended for delivery in the preformed shape and for implantation at a suitable site by a surgeon. As a rule, these materials have no function other than the task of acting as an active compound depot. However, in many cases, such as the management of bone defects, the implant also has to assume supporting or load bearing functions when on removal of parts of bone with malignant affections the stability of the remaining bone is no longer guaranteed, or when in the management of a defect a prosthesis has to be implanted. In these cases, it is additionally essential to be able to adapt the material optimally to the defect.

SUMMARY OF THE INVENTION

Thus, it is an object of the invention to provide a depot material which can be supplied both in a preformed shape and in a form which permits a surgeon to adapt the material optimally to the individual circumstances of use. It is a further object to provide a depot material which is capable of carrying out supporting and load-bearing functions and which, furthermore, also releases the incorporated cytostatic in effective amounts in a reliably reproducible manner.

Upon further study of the specification and appended claims, further objects and advantages of this invention will become apparent to those skilled in the art.

The objects have been achieved by the present invention which provides a composition comprising a drug depot, which can be implanted in the body, for the controlled, delayed release of cytostatics, comprising a synthetic material based on polyacrylates and/or polymethacrylates, containing a cytostatic and at least one amino acid.

The objects are further achieved by providing a precursor for the preparation of a drug depot of this type, which contains about 50 to 75% by weight of a finely divided polymer of acrylic and/or methacrylic esters, which can optionally contain further additives such as, for example, X-ray contrast media, pigments and catalysts, and contains 1 to 15% by weight of an amino acid, 0.1 to 4% by weight of a cytostatic, and 20 to 45% by weight of an acrylic and/or methacrylic ester monomer which optionally contains further additives such as, for example, stabilizers and polymerization accelerators.

The objects of the invention are furthermore achieved by providing a process for the preparation of a drug depot of this type, which is characterized in that about 50 to 75 parts by weight of a finely divided polymer of acrylic and/or methacrylic esters, which can optionally contain further additives such as, for example, X-ray contrast media, pigments and catalysts, and 1 to 15 parts by weight of an amino acid, 0.1 to 4 parts by weight of a cytostatic, and 20 to 45 parts by weight of an acrylic and/or methacrylic ester monomer which optionally contains further additives such as, for example, stabilizers and polymerization accelerators, are mixed to form a semi-solid paste, and the latter is converted into a desired shape and allowed to harden by polymerization and crosslinking.

The objects of the invention are further achieved by providing a method for controlling tumors in mammals comprising implanting a drug depot of the invention in a host.

DETAILED DESCRIPTION

The synthetic materials based on polyacrylates and/or polymethacrylates, which are used as starting materials for the preparation of a drug depot according to the invention, are known per se. An example of one conventional preparation which is preferred is a bone cement which contains in a standard pack 2 bags each containing about 40 g of powder and 2 ampuls each containing 20 ml of liquid. The powder is a fine bead copolymer of methyl methacrylate and methyl acrylate. Such a bone cement is distributed under the trade name Palacos ®.

About 0.5% dibenzoyl peroxide is added to the powder as a catalyst. During the preparation, trace amounts of chlorophyll may be polymerized in to add color in order to more easily identify the material visually.

The powder can optionally also contain, for example, zirconium dioxide as an X-ray contrast medium. The liquid consists essentially of monomeric methyl methacrylate, and about 0.7% dimethyl-p-toluidine as a polymerization accelerator, and traces of hydroquinone as a stabilizer.

This liquid is also, as a rule, colored with traces of chlorophyll for identification. The powder packed in the polyethylene bag is sterilized with ethylene oxide. The liquid is sterilized by filtration and dispensed into glass ampuls.

When two parts by weight of powder are mixed with one part by weight of liquid, the dibenzoyl peroxide reacts with the dimethyl-p-toluidine in the liquid, by which means the radical polymerization is initiated. The mixture is balanced so that it can be used as a doughy paste after only about one minute. This paste remains kneadable for several minutes and then starts to harden, with evolution of heat. The polymerization is essentially complete after about 5 to 10 minutes. During the polymerization, as long as the paste can still be molded, it can be converted into any desired shape, that is to say, for example, introduced directly into the body for filling bone cavities or for cementing in prostheses, or used for the preparation of molded articles which harden outside the body and then can be inserted at any desired point in the body.

The foregoing details on the base cement per se are fully conventional, e.g., as disclosed in U.S. Pat. No. 3,882,858.

According to the invention, a cytostatic is added to this base material. This cytostatic can be admixed as a finely divided powder to the other constituents, that is to say the prepolymer and the monomer, and thus be homogeneously distributed in the resulting polymer. However, it is also possible for it to be incorporated in the prepolymer even during its preparation.

Large numbers of cytostatics are known and, in principle, all can be used according to the invention, as long as they are compatible with the other constituents of the depot and are not decomposed by the heat being produced during the polymerization of the material. Preferred cytostatics include adriamycin, 5-fluorouracil and methotrexate, with methotrexate particularly preferred. These are used to treat tumors for which they are established as effective.

The cytostatic is used in effective amounts, which may differ depending on the active compound used. As a rule, the amount incorporated is such that the concentration resulting in the drug depot is about 0.1 to 4% by weight. Especially with methotrexate, preferred concentrations are 0.2 to 2% by weight and, in particular, 0.4 to 1% by weight.

It is important for reliable release of the active compound that additionally an amino acid is homogeneously incorporated in relatively large amounts of about 1 to 15% by weight to promote the desired release of the active compound. Preferably about 2 to 10% by weight are used, and in particular about 3 to 8% by weight are used. In principle, all natural amino acids which are compatible with the base material and physiologically acceptable are suitable. Preferred are monobasic amino acids with molecular weights of about 75 to 200, such as, for example, glycine, alanine, histidine, leucine, threonine and arginine. Arginine is particularly preferred.

It is especially surprising that not only the amount of amino acid but also its particle size can exert an effect on the release of the cytostatic. Thus, it has been found that particle sizes of, in particular, less than 125 $\mu$m bring about an advantageously uniform and reproducible release. It is possible to use for this purpose commercially available materials from which particles with diameters above 125 $\mu$m have been removed.

However, it has been found, surprisingly, that the good results achieved with a material of this type can be improved further by modification of the shape of the amino acid particles. Thus, a further marked improvement in the release can be achieved by micronization of the particles, the material obtained being in the form of rods and consisting, according to particle analysis by air-jet screening, of at least 95% by weight of particles less than 50 $\mu$m. Conventional micronization methods can be used as described, e.g., in Sucker, Fuchs and Speiser "Pharmazeutische Technologie", Georg Thieme Verlag, Stuttgart, 1978.

The release of the active compound can be improved to an even greater extent by freeze-drying of the amino acid. This results, in the case of arginine, in needle-shaped particles which have a ratio of the smallest to the largest dimension of about 1:2 to 1:20. The length of these particles can be a multiple of 100 $\mu$m, but the thickness is markedly less than 50 $\mu$m as a rule. Conventional freezedrying methods can be used as described, e.g., in Sucker, Fuchs and Speiser "Pharmazeutische Technologie", Georg Thieme Verlag, Stuttgart, 1978.

It is noted that the characterization of a particle by the particle size or the diameter is, strictly speaking, only possible with isometric particles, that is to say, particles which have the same measurements in all three dimensions (spherical in the ideal case). And this is the case with the commercially available material, for example the arginine obtained from E. Merck under Catalogue No. 1542.

It is clear from the examples that an additional improvement in the release of active compound can be achieved by the amino acid particles being reduced in size and/or converted into a shape which substantially differs from the spherical shape. The nominal "diameter" of a particle of this type, for example in the form of a needle or rod, is to be understood to be that of a spherical particle of the same volume. Thus, within the meaning of this definition, a particle in the shape of a rod having a length of about 500 $\mu$m and a thickness of about 50 $\mu$m likewise has a "diameter" of about 125 $\mu$m. Particularly preferred particles have a "diameter" below 50 $\mu$m and the shape of a rod or needle.

The admixture of the amino acid to the base material is carried out analogously to that of the cytostatic, it also being possible to mix the amino acid and cytostatic previous to incorporation of the cytostatic in said base material, or to incorporate the amino acid in the prepolymer.

Although the drug depot according to the invention is primarily used for controlling tumors, it may nevertheless be advantageous to include in the drug depot other additional active compounds, in particular antibiotics and/or antiseptics to control or prevent infections at the site of implantation. Antibiotics should, where possible, be active against both Gram-positive and Gram-negative pathogens and should induce in the pathogens either no or only delayed resistance. Suitable antibiotics include aminoglycoside antibiotics such as amikacin, butirosin, dideoxykanamycin B (DKP), fortimycin, gentamycin, kanamycin, lividomycin, neomycin, netilmicin, ribostamycin, sagamycins, seldomycins and their epimers, sisomicin, sorbistin, tobramycin, streptomycins, linkomycins such as clindamycin, lincomycin and rifamycins such as rifampicin and rifamycin. Examples of suitable antiseptics include bromchlorophen, hexetidine, buclosamide, salicylic acid, cerium nitrate, chlorhexidine, 5-chloro-8-hydroxyquinoline, copper 8-hydroxyquinolate, acridine orange, undecenoic acid, undecoylium chloride, silver salts such as silver sulfadiazine, mafenide, nitrofurazole, cloflucarban, tribromasalan, taurolin and noxythiolin. It is also possible to admix these additional active compounds with the other materials in a manner customary per se, preferably in the form of a finely divided powder, it again being possible, where appropriate, previously to mix them with other individual constituents or to incorporate them in the prepolymer.

These active agents are used in a fully conventional manner and the amounts are easily determinable by one of ordinary skill in the art from only routine experimentation.

As already mentioned, the drug depot according to the invention can be made available completely polymerized and thus in a predetermined shape. This will be the case in particular, when, for example, the only function to be carried out is as a local source of active compound when used in soft tissues. For this purposes, the depot can be prepared in any desired form such as, for example, as granules, cubes, spheres or ellipsoids, or as a film, sheet, pin, tube or other form adapted to the particular use.

However, as a rule the surgeon will be provided with the material according to the invention as the precursor so that molding does not take place until implantation, and thus the drug depot can be adapted optimally to the local circumstances and the material can also be used like a conventional bone cement for the implantation of prostheses.

For this purpose, the constituents are packed ready for use, analogously to the known bone cements described above, in such a manner that the amounts of the solids and the liquid (of the monomer) present in a pack are balanced with respect to one another. It is then possible, in a straightforward manner, to prepare the drug depot from this precursor by mixing the components, the polymerization of the monomer being initiated by the catalyst which is included in the solid component, and the hardened final product being obtained after a reaction time of a few minutes. In the intervening time, during which the material is plastically deformable, it can be introduced into the body and, at the same time, molded.

It is further contemplated that the precursor compositions of the invention may be supplied commercially in the form of each or any one of the components packaged with the cytostatic agent in the form of a kit to be combined with the remaining components, said components either being supplied in the kit or obtained separately.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLE 1

39.2 g of a sterile, fine bead polymer, conisting of a copolymer of methyl acrylate and methyl methacrylate which additionally contains 0.5% dibenzoyl peroxide and traces of chlorophyll, are mixed with 0.8 of L-arginine (substantially isometric particles of a size <125 μm; and 0.5 g of methotrexate, and are packed sterile, together with an ampul containing 20 ml of methyl methacrylate with the addition of about 0.7% dimethyl-p-toluidine and about 0.006% hydroquinone (monomer liquid), to form a unit ready for use.

The process in the following examples is analogous, the following amounts of the starting materials being used:

EXAMPLE 2

38.0 g of bead polymer, 2.0 g of L-arginine, 0.5 g of methotrexate and 20.0 ml of monomer liquid.

EXAMPLE 3

37.0 g of bead polymer, 3.0 g of L-arginine, 0.5 g of methotrexate and 20.0 ml of monomer liquid.

EXAMPLE 4

36.0 g of bead polymer, 4.0 of L-arginine, 0.5 g of methotrexate and 20.0 ml of monomer liquid.

EXAMPLE 5

34.0 g of bead polymer, 6.0 g of L-arginine, 0.5 g of methotrexate and 20.0 ml of monomer liquid.

EXAMPLE 6

37.0 g of bead polymer, 3.0 g of L-arginine, 0.1 g of methotrexate and 20.0 ml of monomer liquid.

EXAMPLE 7

37.0 g of bead polymer, 3.0 g of L-arginine, 0.25 g of methotrexate and 20.0 ml of monomer liquid.

EXAMPLES 8 to 14

The process is analogous to that of Examples 1 to 7, the arginine being used in a micronized form with a particle diameter below 50 μm.

EXAMPLES 15 to 21

The process is analogous to that of Examples 1 to 7, the arginine being used in the freeze-dried form (needles) with a particulate diameter below 125 μm.

EXAMPLES 22 to 42

The process is analogous to that of Examples 1 to 7, in each case L-histidine, L-leucine or L-threonine being used in place of arginine.

EXAMPLES 43 to 49

The process is analogous to that of Examples 1 to 7, 0.5 g of gentamycin additionally being admixed to the solids.

EXAMPLES 50 to 56

The process is analogous to that of Examples 1 to 7, 0.25 g of gentamycin additionally being admixed to the solids.

EXAMPLE 57

A paste is prepared from a precursor according to Example 4, by mixing the solid component with the monomer liquid, and is introduced or injected, manually or with the aid of a gun, into a bone cavity and is allowed to harden there.

The precursors according to the remaining Examples 1 to 56 can be used in the same way.

It is possible to push a prosthesis, such as, for example, an endoprosthesis, into the paste which has been introduced into the body but has not yet hardened. The prosthesis is solidly anchored in the body after the synthetic material has hardened.

EXAMPLE 58

36 g of a finely divided copolymer of methyl acrylate and methyl methacrylate, which additionally contains 0.5% dibenzoyl peroxide and traces of chlorophyll, and 4 g of micronized L-arginine, 0.5 g of methotrexate, 0.5 g of gentamycin and 20 ml of methyl methacrylate, which contains about 0.7% dimethyl-p-toluidine and about 0.006% hydroquinone, are thoroughly mixed. The resulting paste is used to shape spheres, pins and ovoids as well as larger implants, such as cylinders, tubes, sheets, films and other articles of any desired shape and size, which have hardened after a few minutes. The articles are packed sterile and can be used as local active compound depots.

Precursors according to Examples 1 to 56 can be processed to molded articles in an analogous manner.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A drug depot composition comprising a base of a polyacrylate or polymethacrylate, an amount of an amino acid effective to control the release of the drug from the composition and an effective amount of a cytostatic agent, wherein the amino acid is in the form of particles of a size less than 125 μm.

2. A drug depot composition of claim 1 comprising 1-15% b.w of an amino acid.

3. A composition according to claim 1, further comprising an antibiotic or antiseptic agent.

4. A composition according to claim 1, wherein the cytostatic agent is adriamycin, 5-fluorouracil or methotrexate.

5. A composition according to claim 4, wherein the cytostatic agent is methotrexate.

6. A composition according to claim 1, wherein the cytostatic agent is present in an amount of 0.1-4% b.w.

7. A composition according to claim 1, wherein the cytostatic agent is present in amount of 0.2-2% b.w.

8. A composition according to claim 1, wherein the amino acid is a monobasic natural amino acid having a molecular weight of about 75-200.

9. A composition according to claim 8, wherein the amino acid is glycine, alanine, histidine, leucine, threonine or arginine.

10. A composition according to claim 4, wherein the amino acid is arginine.

11. A composition according to claim 1, wherein the amino acid is a monomeric amino acid.

12. A composition according to claim 1, wherein the amino acid particles are rod-shaped and at least 95% have a nominal diameter of less than 50 μm.

13. A composition of claim 1, wherein the amino acid particles are freeze dried particles.

14. A composition of claim 9, wherein the amino acid particles are freeze dried particles.

15. A kit for the preparation of a drug depot, having as components a polyacrylate or polymethacrylate base comprising an effective amount of a cytostatic agent, and at least one of a polymer of an acrylic or methacrylic ester, an amino acid, an acrylic or methacrylic ester monomer, or a polymerization catalyst, whereby the components may be combined to form a bone cement or a component for the preparation of a bone cement.

16. A kit according to claim 15, comprising an effective amount of a cytostatic agent, a polymer of an acrylic or methacrylic ester, an amino acid, an acrylic or mthacrylic ester monomer, and a polymerization catalyst.

17. A kit according to claim 16, further comprising an antibiotic or antiseptic agent.

18. A kit according to claim 16, wherein the cytostatic agent is adriamycin, 5-fluorouracil or methotrexate.

19. A composition according to claim 14, wherein the amino acid is a monobasic natural amino acid having a molecular weight of about 75-200 .

20. A method of achieving a depot effect in the administration of a cytostatic agent to a patient comprising administering said agent to the patient in the form of a drug depot of claim 1.

21. A method for locally treating a tumor in a patient comprising implanting in the patient a drug depot of claim 1 at the locus of the tumor.

* * * * *